United States Patent [19]

Vreeswijk et al.

[11] Patent Number: 4,937,320
[45] Date of Patent: Jun. 26, 1990

[54] DIMERIZED FATTY ACID HAVING A HIGH CONTENT OF DICARBOXYLIC ACID

[75] Inventors: Johannes J. Vreeswijk, Rotterdam; Klaus D. Haase, The Hague, both of Netherlands

[73] Assignee: Unilever Patent Holdings B.V., Rotterdam, Netherlands

[21] Appl. No.: 304,599

[22] Filed: Feb. 1, 1989

Related U.S. Application Data

[62] Division of Ser. No. 83,195, Aug. 10, 1987.

[30] Foreign Application Priority Data

Apr. 13, 1987 [NL] Netherlands .................... 8700862

[51] Int. Cl.$^5$ ............................................... C08G 63/02
[52] U.S. Cl. ................................. 528/272; 528/295.3; 528/332; 528/501
[58] Field of Search ............... 528/272, 295.3, 332, 528/501

[56] References Cited

U.S. PATENT DOCUMENTS

| | | | |
|---|---|---|---|
| 2,793,219 | 5/1957 | Barrett et al. | 260/407 |
| 2,955,121 | 10/1960 | Myers et al. | 260/407 |
| 2,964,545 | 12/1960 | Harrison | 260/407 |
| 3,900,436 | 8/1975 | Drawert et al. | 528/288 |
| 4,045,389 | 8/1977 | Drawert et al. | 528/324 |
| 4,396,759 | 8/1983 | Drawert et al. | 528/339.3 |
| 4,397,991 | 8/1983 | Drawert et al. | 525/167 |
| 4,480,086 | 10/1984 | O'Neill | 528/295.3 |

FOREIGN PATENT DOCUMENTS 999732 7/1965 United Kingdom.
1050148 12/1966 United Kingdom.

*Primary Examiner*—Morton Foelak
*Assistant Examiner*—S. A. Alquah
*Attorney, Agent, or Firm*—Cushman, Darby & Cushman

[57] ABSTRACT

The invention provides a dimerized fatty acid with a content of dicarboxylic acid of at least 97.5 wt. %, preferably at least 98.5 wt. %.

Also provided is a process for the preparation of a pure dimerized fatty acid in which a fatty acid that has been dimerized is freed, by a physical method, of fractions having predominantly monocarboxyic acids and tricarboxylic acids.

The invention further provides a high molecular weight polymer which contains groups derived from a $C_4$–$C_{12}$ dicarboxylic acid and approximately equimolar amounts of dicarboxylic acids and diamines and/or diols which are converted while volatile reaction products are removed.

7 Claims, No Drawings

DIMERIZED FATTY ACID HAVING A HIGH CONTENT OF DICARBOXYLIC ACID

This is a division of application Ser. No. 07/083,195, filed Aug. 10, 1987.

The application relates to dimerised fatty acids having a high content, i.e. at least 97.5 wt. %, of dicarboxylic acid, as well as to polymers which contain groups derived from such pure dimeric fatty acids. As such polymers, especially polyamides, polyesters, polyesteramides and polyether-amides are meant, but also polyurethan for example.

The commercially available dimerised fatty acids mostly contain approximately 15 to 25 wt. % trimer (T) and higher oligomers and 1 to 5 wt. % monomer (M) and the remainder is often regarded as dimer (D). The terms monomer, dimer and trimer are in this case based more on the molecular weight than on the functionality, i.e. the number of carboxyl groups per molecule. Therefore, a dimeric fatty acid that has lost a carboxyl group through decarboxylation is regarded here as dimer (D), while according to the present application it does not count as dicarboxylic acid but, on the contrary, is regarded as monocarboxylic acid.

Furthermore, from GB-A- 999 732 (General Mills Inc.) purified polymeric fatty acids are known which are "water white" and have a relatively high content of dimer (D), as that is determined by short way distillation of polymerised fatty acids according to Paschke (J.A.O.C.S. 31 (1954), 5–7). According to this method, however, among other things a certain amount of cracking of the residue takes place, as a result of which the percentages of trimer determined in this way are lower than in reality. A more reliable method of determining the contents of monocarboxylic acid, dicarboxylic acid and tricarboxylic acid is by means of gas-liquid chromatography (GLC) as described in the thesis of M.J.A.M. den Otter, The clay-catalyzed dimerisation of oleic acid, pages 52–55, Technische Hogeschool Eindhoven, The Netherlands, 1968.

The methodology of GLC determination described in this thesis was also used according to the present application and gives values which are directed to the number of carboxyl groups rather than to the molecular weight. The percentages of trimer in the British patent application cited are consequently considerably lower than the percentages of tricarboxylic acid which are determined by the GLC method and differences of several percent have been observed. The percentages of trimer mentioned in this patent application on page 7 are considered to be unrealistically low and the products mentioned there are consequently not damaging to the novelty of the dimeric fatty acids having a weight percentage of more than 97.5 or of the 98.5 of dicarboxylic acid according to the present invention. Also in EP-A- 22 048 (Rhone Poulenc Ind.) polyamides are disclosed which are based on hydrogenated, fractionated, polymerised fatty acids which are said to contain more than 95% by weight of "dimer". These polyamides allegedly have favourable properties like: homogeneity, transparency, toughness, hydrolysis stability and thermal resistance.

The present application now claims rights for, inter alia, a dimerised fatty acid having a dicarboxylic acid content of more than 97.5% by weight, preferably more than 98.5% by weight, more preferably more than 99.0% by weight. Dimerised fatty acids having such high contents of dicarboxylic acid can be obtained by fractionation, with a physical method, of a fatty acid that has been dimerised according to a method known per se until a fraction has been obtained having the desired percentage of dicarboxylic acid.

For the dimerisation of fatty acids, as a rule unsaturated fatty acids—or mixtures thereof—are used which contain 16 to 22 carbon atoms in the molecule.

The dimerisation normally takes place at temperatures between 180° and 270° C. under water vapour pressure and in the presence of approximately 2 to 10% clay catalyst. This process is also described in GB-A-1 050 148 (General Mills Inc.). The fractionation of the dimerised product can be effected in various ways, but distillation under high vacuum at increasing temperature (molecular distillation) is a suitable method. Extraction methods can also be used, in particular supercritical extraction. Optionally, the dimerised fatty acid can also be hydrogenated, as described, for example, in GB-A- 999 730.

The present application furthermore claims rights for polymers, particularly high polymeric materials, in which dimerised fatty acid having a percentage of more than 97.5, preferably more than 98.5% or more preferably even more than 99.0% of dicarboxylic acid has been incorporated. This dicarboxylic acid that, depending on the starting fatty acid, contains from 32 to 44 carbon atoms in the molecule, imparts to a high polymer, in the purity mentioned, an exceedingly favourable combination of mechanical properties, such as a good tensile strength and elasticity, good low temperature impact resistance and the good dimension stability because of low water absorption. Thus it has been found, for example, that the tensile strength of a polyamide based on hexamethylenediamine and dimer having 99% dicarboxyl acid is much better than that of a corresponding polyamide based on dimer having 95% dicarboxylic acid; also with respect to flexibility, the first polymer is better than the second.

In order to obtain favourable properties in the polyamide, for e.g. hot-melt bonding, it is sometimes desirable to prepare polyamides with combinations of diamines, for example combinations of ethylenedamine (EDA) and hexamethylenediamine (HMDA), namely in ratios of 20/80 to 80/20, preferably in ratios of 60/40 to 40/60 molar.

Also aromatic amines like piperazine can be used in addition in order to obtain special effects. As a rule the diamine contains 2 to 9 carbon atoms. For high-quality plastics it is particularly advantageous to include caprolactam in the polyamide.

Besides the pure dimer according to the present invention, another (co-) dicarboxylic acid can be used. Suitable dicarboxylic acids are particularly those which contain between 4 and 12 carbon atoms, both aliphatic and aromatic dicarboxylic acids being suitable. Here the molar ratio between dimeric acid according to the invention and other dicarboxylic acid lies between 20/80 and 80/20, preferably between 60/40 and 40/60. Besides diamines, also difunctional ether-amines and ester-amines or blocks thereof can be built in. Both high molecular polyamides and lower, reactive polyamides having, for example, terminal carboxyl groups are encompassed.

The present application also provides polyesters, in particular high molecular polyesters, which contain dimerised fatty acid according to the present invention, as well as $C_2$–$C_6$ diols, optionally together with other above-mentioned dicarboxylic acids; polyether diols can also be incorporated in addition. For these high polymers, attention is drawn in particular to the favourable combination of a high melting viscosity and good flexibility. Besides high polymeric polyesters, the present invention also provides lower molecular polyesters having terminal carboxyl groups, which can be excellently hardened with polyepoxides to particularly good, flexible coatings.

The polymers, particularly the high molecular weight polymers, according to this embodiment of the invention can be prepared in a manner known per se by converting dimeric fatty acids having a high content of dicarboxylic acid (or a functional derivative thereof such as, for example, dimethylester) with at least one diamine/diol and/or ether diamine, optionally in the presence of another dicarboxylic acid, while removing the volatile components formed, such as water or methanol.

Unlike the case with the preparation of the conventional polymers, it is noticeable with this process that, during the cooking, there is little or rather no danger of the reaction mixture starting to gel and thus becoming unmanageable or of the molecular weight not being able to increase sufficiently because of the presence of too much monocarboxylic acid. For the preparation of high polymers, of course, equimolar amounts of dicarboxylic acid and diamine/diol and optionally ether diol are used, or sometimes a small excess of volatile reaction component, which excess is eventually distilled off.

The invention is illustrated by the following examples:

EXAMPLE 1

The commercially available dimerised fatty acid PRIPOL 1017, ex Unichema, Gouda, was separated via a so-called molecular distillation into a fraction which contained mainly difunctional fatty acids. The separation of the monofunctional material was carried out at a temperature of 240° C. and a pressure of 0.005 mm Hg, while hereafter the difunctional carboxylic acid was distilled over at a temperature of 280° C. and a pressure of 0.002 mm Hg. This fraction was hydrogenated with a Pd on carbon carrier as catalyst at a pressure of 2.5 MPa and a temperature of 180° C. for 5 hours. The hydrogenated product was subsequently separated again with the aid of a so-called molecular distillation apparatus. During the molecular distillation, first of all monofunctional fatty acids were separated at a temperature of 280° C. and a pressure of 0.001 mm Hg. In Table 1 the compositions of the most important products after the different process steps are summarized.

TABLE 1

| | PRIPOL 1017 | fraction after molecular distillation | |
|---|---|---|---|
| | | first time | second time |
| less than difunctional (wt. %) | 7.1 | 2.5 | 0.5 |
| difunctional (wt. %) | 72.0 | 93.5 | 99.0 |
| higher than difunctional (wt. %) | 21.0 | 4.0 | 0.5 |
| iodine value (Weiss) | 98 | 98 | 9 |

EXAMPLES 2–7

A commercial product comparable with those described in BG-A-999 732 is PRIPOL 1010 (ex Unichema, Gouda), that has the composition as given in Table 2.

TABLE 2

| | PRIPOL 1010 (composition in wt. %) |
|---|---|
| less than difunctional | 1.5 |
| difunctional | 95.5 |
| higher than difunctional | 3.0 |
| iodine value (Weiss) | 6 |

Polyamides were prepared from the above-mentioned purified, dimerised fatty acids. The process for the preparation of these polyamides is: reacting the dimerised fatty acid for 5 hours at 220° C. with an equivalent amount of diamine, using 0.03 wt. % phosphoric acid as catalyst and applying a vacuum of 20 mm Hg for the last hour.

The following polyamides were prepared (Table 3):

TABLE 3

| | Type dimer | Type amine | amounts used (grams) | |
|---|---|---|---|---|
| | | | dimer | amine |
| 1 | 1010 | EDA | 507.6 | 53.6 |
| 2 | (*) | EDA | 507.6 | 53.6 |
| 3 | (*) | EDA | 507.6 | 53.6 |
| 4 | (*) | HMDA (60%) | 400 | 136.5 |
| 5 | 1010 | HMDA (60%) | 400 | 136.5 |

(*)dimer as prepared according to Example 1.

The most important characteristics of the polyamides are summarized in Table 4.

TABLE 4

| Ex. | Acid value | Amine value | Viscosity (Pas) at 230° C. | Viscosity (Pas) at 190° C. | Processing temp. °C. | Tensile strength at rupture MPa | Elasticity (%) |
|---|---|---|---|---|---|---|---|
| 1 | 2.8 | 1.8 | -12 | 39 | 110 | 26 | 470 |
| 2 | 1.8 | 2.2 | 21 | 103 | 114 | 35 | 550 |
| 3 | 3.5 | 1.3 | 18 | 76.5 | 115 | 36 | 550 |
| 4 | 3.3 | 0.7 | 89 | 290 | 92 | 35 | 540 |

We claim:
1. A polymer that contains groups derived from dimerised fatty acid, in which the dimerised fatty acid groups consist of at least 97.5 wt. % of dicarboxylic acid radicals.

2. A high polymer according to claim 1, in which the dicarboxylic acid groups are built into a polyamide.

3. A polyamide according to claim 1, in which the polyamide contains groups of a $C_2$–$C_9$ alpha-omega-diamine.

4. A high molecular weight polymer according to claim 1, in which the dicarboxylic acid groups are built into a polyester.

5. A high polymer according to any one of the claims 1, 2 or 4, in which the polymer also contains groups derived from a $C_4$–$C_{12}$ dicarboxylic acid.

6. A high polymer according to claim 1, in which the polymer contains in the chain not only amide groups but also ester and/or ether groups.

7. A process for the preparation of a polymer according claim 1, wherein approximately equimolar amounts of dicarboxylic acids and diamines and/or diols are converted with each other while volatile reaction products are removed until the desired polymer has been obtained, characterized in that the dicarboxylic acid consists at least partly of dimerised fatty acids having a content of more than 97.5 wt. % dicarboxylic acid.

* * * * *